United States Patent [19]

Wei et al.

[11] 4,419,516

[45] Dec. 6, 1983

[54] ANTIVIRAL IMIDAZO- AND TRIAZOLO-PYRIDINES

[75] Inventors: Peter H. L. Wei, Springfield; Stanley C. Bell, Penn Valley, both of Pa.

[73] Assignee: American Home Products Corporation, New York, N.Y.

[21] Appl. No.: 388,805

[22] Filed: Jun. 16, 1982

[51] Int. Cl.³ .......................................... C07D 471/04
[52] U.S. Cl. ................................. 546/119; 546/121
[58] Field of Search ............................... 546/119, 121

[56] References Cited

U.S. PATENT DOCUMENTS 4,361,567 11/1982 Bristol et al. ...................... 424/256

*Primary Examiner*—Richard Raymond
*Assistant Examiner*—Bernard Dentz
*Attorney, Agent, or Firm*—George Tarnowski

[57] ABSTRACT

Thioacetonitrile of imidazo- and triazolo pyridines and their use as antiviral agents are disclosed.

3 Claims, No Drawings

ANTIVIRAL IMIDAZO- AND TRIAZOLO-PYRIDINES

The invention relates to thioacetonitrile and derivatives of imidazo- and triazolo-pyridines and their use as antiviral agents.

The invention is directed to novel compounds having the general formula

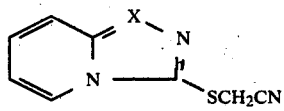

wherein X is CH or N.

The compound having the formula

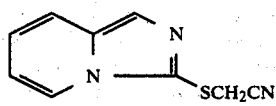

can be prepared by reacting imidazo[1,5-a]pyridine-3(2$\underline{H}$)-thione of the formula

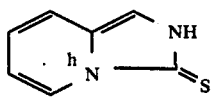

with chloroacetonitrile to furnish the desired thioacetonitrile derivative. The starting imidazo[1,5-a]pyridine-3(2$\underline{H}$)-thione can be prepared according to the following reaction sequence:

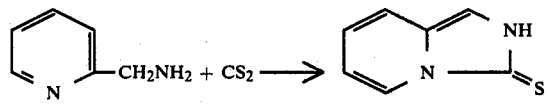

In another preparation N-phenyl-N'-2-pyridinylmethylthiourea, prepared by reacting phenylisothiocyanate with 2-aminomethylpyridine, is converteed to imidazo[1,5-a]pyridine-3(2$\underline{H}$)-thione by heating in xylene:

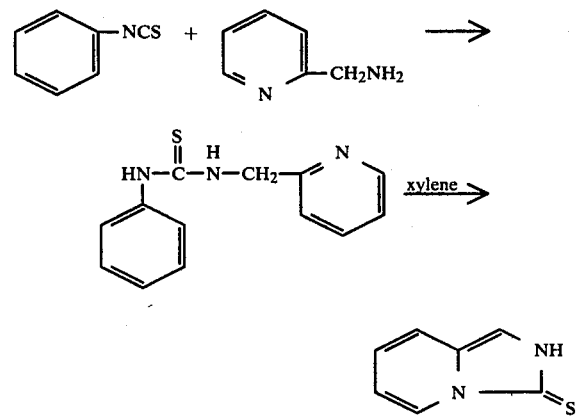

The compound of the formula

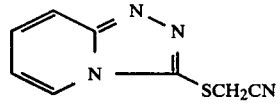

can be prepared by reacting 3-mercapto-1,2,4-triazolo[4,3-a]-pyridine with chloroacetonitrile. The starting 3-mercapto-1,2,4-triazolo[4,3-a]pyridine can be prepared according to the method of Tarbell, J.Am.-Chem.Soc. 70, 1381-5 (1948).

The compounds of the invention have antiviral activity and can be used against RNA viruses in humans and other mammals. For this purpose, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart antiviral activity thereto on oral administration. The compounds may also be injected parenterally, in which case they are used in the form of a sterile solution containing other solutes, for example, enough saline or glucose to make the solution isotonic.

The antiviral activity of the compounds of the invention may be demonstrated in standard procedures which are more fully described in the examples given hereinafter.

The following examples show the preparation of the compounds of the invention.

EXAMPLE 1

Imidazo[1,5-a]pyridine-3(2$\underline{H}$)-thione

A. To 1.6 g (0.15 m) 2-aminomethylpyridine and 16 g triethylamine in 250 ml methanol is slowly added 65 ml carbon disulfide. The solution is heated to reflux overnight, and after the solvent is removed, the residual solid is dissolved in 250 ml 0.5 N sodium hydroxide solution. The compound is reprecipitated with acetic acid as a maroon solid which weighs 12 g. The crude material is purified by first dissolving in methylene chloride, treatment with Darco and reprecipitation by removal of the solvent. The compound has a decomposition point of 147°-53° C.

Analysis for: $C_7H_6N_2S$, Calculated: C, 55.97; H, 4.03; N, 18.66; S, 21.35, Found: C, 55.86; H, 4.02; N, 18.44; S, 21.03.

B. N-Phenyl-N'-2-pyridinylmethylthiourea is prepared by heating 19.8 g (0.147 m) phenylisothiocyanate and 13.2 g (0.122 m) 2-aminomethylpyridine in 500 ml benzene for 3 hr. The solid (22.8 g, 77% yield) which is collected with a melting point of 98°-9° C. and is analytically pure.

Analysis for: $C_{13}H_{13}N_3S$, Calculated: C, 64.17; H, 5.38; N, 17.27; S, 13.18 Found: C, 64.56; H, 5.39; N, 17.40; S, 13.09.

N-Phenyl-N'-2-pyridinylmethylthiourea is converted to imidazo[1,5-a]pyridine-3(2$\underline{H}$)-thione in 80% yield by heating in xylene.

EXAMPLE 2

3-Mercaptopyrido[2,1-c]-S-triazole 5 g of 2-pyridylhydrazine (prepared by heating 2-chloropyridine with 85% hydrazine hydrate at 125° C. for 24 hours) is added to 12 ml of carbon disulfied in 40 ml of chloroform. A precipitate is formed, and the mixture is refluxed on a steam bath for twenty hours, with the evolution of hydrogen sulfide. The crystalline material is isolated given 6.1 g (88% yield) of title compound which has a m.p. of 209°–210° C.

Analysis for: $C_6H_6N_3S$, Calculated: C, 47.7; H, 3.3, Found: C, 48.1; H, 3.4.

EXAMPLE 3

(Imidazo[1,5-a]pyridin-3-ylthio)acetonitrile 51.0 g (0.315 m) imidazo[1,5-a]pyridine-3(2H)-thione, prepared according to Example 1, 27.6 g (0.365 m) chloroacetonitrile and 30.7 g triethylamine are dissolved in 600 ml of toluene and the solution is heated to reflux for 3 hr, then allowed to cool to room temperature. The toluene solution is washed with water, dried over anhydrous magnesium sulfate and treated with Darco. After the solvent is removed, the residual solid is recrystallized from cyclohexane. A total yield of 62 g is obtained. The recrystallized sample has a melting point of 120°–2° C.

Analysis for: $C_9H_7N_3S$, Calculated: C, 57.16; H, 3.73; N, 22.22; S, 16.96, Found: C, 57.15; H, 3.73; N, 22.31; S, 16.67.

EXAMPLE 4

(1,2,4-Triazolo[4,3-a]pyridin-3-ylthio)-acetonitrile

Following the procedure of Example 3, and substituting 3-mercapto-1,2,4-triazolo[4,3-a]pyridine, prepared according to Example 2, for imidazo[1,5-a]pyridine-3(2H)-thione, the title compound is prepared in 52% yield. The compound, after recrystallization from a mixture of benzene-acetonitrile, melts at 121°–3° C.

Analysis for: $C_8H_6N_4S$, Calculated: C, 50.55; H, 3.18; N, 29.48; S, 16.87, Found: C, 50.50; H, 3.23; N, 29.85; S, 16.88.

EXAMPLE 5

The compounds of the invention are tested in vivo against RNA viruses Influenza B-Mass. and $A_2$ Taiwan according to the following protocol:

Ten 12-14 gm. mice are treated with each dilution of a test compound 24 hours prior to and at 1, 24, 48 and 72 hours after the inoculation of a standardized challenge dose of test virus. Mice are inoculated intraperitoneally with the compound dilution and intranasally with either of the two Influenza viruses and subcutaneously with compound dilution and intraperitoneally with Herpes virus. Twenty mice, inoculated with saline instead of the test compound, serve as the control group. All mice are observed for 21 days and the number of deaths occurring in each group recorded. Antiviral activity of a compound is scored statistically for significance at the 95 and 99% confidence levels on the basis of percentage of survivors and prolongation of life.

In this test, the compound (1,2,4-triazolo[4,3-a]-pyridin-3-ylthio)acetonitrile showed significant activity against Influenza $A_2$ Taiwan, while the compound (imidazo[1,5-a]-pyridin-3-ylthio)acetonitrile showed significant activity against Influenza B-Mass.

What is claimed is:

1. A compound having the formula

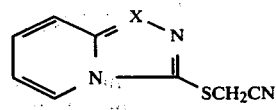

wherein X is CH or N.

2. The compound of claim 1, which is (imidazo[1,5-a]-pyridin-3-ylthio)acetonitrile.

3. The compound of claim 1, which is (1,2,4-triazolo-[4,3-a]pyridin-3-ylthio)acetonitrile.

* * * * *